United States Patent [19]

Amotz et al.

[11] 4,116,771

[45] Sep. 26, 1978

[54] IMMOBILIZED SACCHARIFYING ENZYME PRODUCT AND PROCESS FOR PREPARATION THEREOF

[75] Inventors: Shmuel Amotz, Ganloese; Tage Kjaer Nielsen, Herlev; Poul Borge Rosenius Poulsen, Vaerloese; Barrie Edmund Norman, Farum, all of Denmark

[73] Assignee: Novo Industri A/S, Bagsvaerd, Denmark

[21] Appl. No.: 810,788

[22] Filed: Jun. 28, 1977

[51] Int. Cl.$^2$ .............................................. C07G 7/02
[52] U.S. Cl. .................................... 195/63; 195/68; 195/DIG. 11
[58] Field of Search .................. 195/63, 68, DIG. 11

[56] References Cited

U.S. PATENT DOCUMENTS

| 3,838,007 | 9/1974 | van Velzen | 195/68 X |
| 3,972,776 | 8/1976 | Vieth et al. | 195/63 X |
| 3,980,521 | 9/1976 | Amotz et al. | 195/68 |
| 4,011,137 | 3/1977 | Thompson et al. | 195/31 R |

*Primary Examiner*—Lionel M. Shapiro
*Attorney, Agent, or Firm*—Fidelman, Wolffe, and Waldron

[57] ABSTRACT

An immobilized saccharifying enzyme product formed by coating granular casein with a liquid-permeable proteinaceous layer comprising saccharifying enzyme and egg albumen cross-linked by reaction with glutaraldehyde.

18 Claims, No Drawings

IMMOBILIZED SACCHARIFYING ENZYME PRODUCT AND PROCESS FOR PREPARATION THEREOF

This invention relates to insolubilized enzymes and to a process for preparing insolubilized enzyme products.

More particularly, this invention relates to particulate physically stabilized forms of insolubilized saccharifying enzymes selected from the group consisting of amyloglucosidase and maltogenic alpha-amylase, both usually of fungal origin, and to a process for the preparation of such insolubilized enzyme products.

BACKGROUND OF THE INVENTION

Insolubilization (or immobilization) of extracellular and of intracellular water soluble enzymes, that is, the fixation of catalytically active (native enzymes in an insolubilized, solid or quasisolid, shaped or technological structure has become of increasing technoligical and economic importance, as a means of rendering a particular enzyme product reusable in batch-type processes or suitable for a continuous mode of operation in a socalled enzyme reactor.

During recent years efforts have been devoted to the development of immobilization technology in the starch processing industry in connection with the manufacture of such products as high dextrose and high fructose syrups. Lately, the relative importance of the latter has been increasing in food and related industries, high fructose syrup being an advantageous substitute for sucrose and for (the less sweet) high dextrose syrup. Two additional types of sugar syrup based on starch hydrolysis having a substantial content of maltose, namely high maltose and high conversion syrup are being used to an increasing extent, particularly in the confectionary (hard candy) and canning industries, respectively.

The over-all industrial process of converting starch via high dextrose syrup into high fructose syrup comprises three consecutive steps, namely the starch thinning or liquefaction process to dextrins, catalyzed by acid and/or by a bacterial alpha-amylase, followed by saccharification to a high dextrose syrup and then the conversion of the latter into high fructose syrup, each process catalyzed by its specific enzyme, viz. amyloglucosidase and glucose isomerase, respectively. Whereas the most recent technological development has made continuous processes available for both the first and the third step of the above production sequence, industrial saccharification is still predominantly a batch-type process. The starting material of a high maltose type of syrup is also liquefied starch produced by either one of the methods just described. However, in this case the subsequent saccharification step resulting in a syrup of high maltose content (and usually containing relatively little glucose) is effected by means of a maltogenic amylase, preferably a fungal alpha-amylase. Like glucogenic saccharification, the corresponding maltogenic process is usually conducted batch-wise using the soluble enzyme.

Although the convenience of having at ones disposal a totally continuous production sequence is evident, the development of industrial enzyme reactor techniques involving the use of insolubilized amyloglucosidas in the saccharification step is only at a preliminary stage.

The prior art contains a number of references to the insolubilization of amyloglucosidase, or example by bonding the enzyme to insoluble inorganic or organic carriers. However, only few of these methods appear to have been developed beyond the laboratory bench scale. Among the methods that apparently have passed that stage specific mention should be made of the immobilization of amyloglucosidase by covalent bonding to porous particles of glass or ceramic material. In this connection reference is made to a recent article published by D. D. Lee et al. in "Die Starke", Vol. 27 (1975pp 384-387.

In a continuous process in which a pilot plant size column was packed with this particular enzyme product and fed with solutions of commercially available dextrins, degrees of conversion to dextrose were attained which approached the minimal conversion of about 92 percent generally required in a batch saccharification process with soluble amyloglucosidase, although a conversion to above 93 percent is of course preferred. However, product analyses indicated that reversion reactions, i.e. amyloglucosidase catalyzed repolymerization of glucose into maltose, isomaltose and higher oligomers, occur to a greater extent in the column process that in the batch-type, free enzyme process.

The phenomenon of increased reversion encountered with an immobilized enzyme product of this type appears at least partly to be an inherent disadvantage of using porous enzyme carrier materials. Clearly, the porous structure contributes substantially to the total surface area lending itself to enzyme bonding and, consequently, to the maximal enzyme activity obtainable from the immobilized enzyme product.

However, the high concentration of amyloglucosidase attached to the carrier pore surface combined with a reduced diffusion rate within the pores inevitably results in locally high glucose concentrations, thus constituting favourable conditions for the promotion of enzyme processes having high $K_m$-values. This is exactly the case with the undesirable reversion reactions, and particularly those in which isomaltose and isomaltriose are formed.

An insolubilized maltogenic alpha-amylase product, prepared by bonding the soluble enzyme to aminoethylcellulose by means of glutaraldehyde, is disclosed in U.S. Pat. No. 4,011,137 (Thompson et al.). However, according to this reference the intended use of the immobilized enzyme is limited to increasing the degree of conversion of dextrinized starch to glucose by means of a similarly immobilized amyloglucosidase preparation, the saccharification process being conducted by means of a mixture of the two immobilized enzymes. There is no demonstration whatsoever in the patent of the use of the immobilized maltogenic alpha-amylase for the production of a high maltose syrup.

An additional disadvantage of using a particulate immobilized saccharifying enzyme, in which the enzyme is bonded to a porous or reticular material which is essentially homogeneous throughout the particulate structure can be expected from the heterogeneity in molecular size of the dextrinized starch serving as substrate. All dextrins, whether produced by acid or by enzymatic hydrolysis of starch, contain substantial fractions of different glucose oligomers. Normally, the starch thinning process is stopped when the average chain length of the hydrolysate is in the range of from 6 to 10 glucose residues, and it is conceivable that steric hindrance may impede the diffusion of the larger dextrin molecules to enzyme sites embedded beyond a certain depth within the porous or reticular particle structure.

It is one object of the present invention to overcome or at least to mitigate the principal disadvantages encountered with the prior art immobilized saccharifying enzyme products described above, by providing an insolubilized product having process characteristics essentially similar to those of the soluble enzyme, irrespective of whether the immobilized product is used in a batch process or in a continuous mode of operation.

In the case of immobilized amyloglucosidase this requirement normally entails that a continuous saccharification process can be conducted under industrial process conditions (i.e. in terms of composition and flow rate of the dextrin feed) so as to yield a glucose concentration of at least 92 percent, the total concentration of disaccharides (maltose and isomaltose) and trisaccharides (mainly panose and isomaltotriose) not exceeding about 4 and 1 percent, respectively.

In the case of the immobilized maltogenic alpha-amylase the corresponding conversion parameters required would be: approximately 40–60 percent maltose, 25–35 percent maltotriose and, preferably, less than 10 percent glucose.

Since commercially available soluble saccharifying enzymes are relatively cheap and highly active, another preferable but not essential object of the present invention is the provision of economically favourable, insolubilized products. The pursuance of this goal necessitates the utilization of comparatively inexpensive, commercially available carrier and other auxiliary materials and, furthermore, the achievements of substantial recoveries of enzyme activity in the immobilization process. In addition, from a toxicological point of view all materials used should be acceptable for food processing purposes.

Briefly, these objects are attained according to the present invention which provides an immobilized saccharifying enzyme product in particulate form in which enzymatically inert, water-insoluble carrier particles are coated with a liquid-permeable, proteinaceous layer in which the saccharifying enzyme is immobilized by cross-linking with glutaraldehyde.

Attempts to prepare such insolubilized products in which the proteinaceous layer is composed of the glutaraldehyde cross-linked saccharifying enzyme alone proved unsuccessful in the sense that, irrespective of the choice of core material, they resulted in incompletely immobilized products from which the enzyme would rapidly leak away. Similar problems were encountered with a variety of water-insoluble particulate carrier materials of inorganic (for example mineral or ceramic) origin and with certain types of proteinaceous core material (such as granular soy protein), apparently because of an insufficient number of cross-link binding sites at the surface of such particles.

BRIEF DESCRIPTION OF THE INVENTION

However, it has now been found that the physical and enzymatic properites of the immobilized enzyme coated products can be greatly improved, provided that granular casein is used as core material and, furthermore, that glutaraldehyde cross-linking of the enzyme in the coating layer is effected in the presence of the water-soluble, non-enzymatic binder protein egg albumen, such materials evidently constituting a favourable combination for creating a sufficient number of inter-protein enzyme stabilizing cross-links.

Thus, more specifically, according to one aspect of the present invention there is provided an immobilized saccharifying enzyme product in particulate form, the saccharifying enzyme being selected from the group consisting of amyloglucosidase and maltogenic alpha-amylase, which product comprises carrier particles of granular casein having a coating of a liquid-permeable proteinaceous layer comprising the saccharifying enzyme and egg albumen cross-linked by reaction with glutaraldehyde.

THE INVENTION IN DETAIL

The relative amounts of the constituent saccharifying enzyme, casein and albumen may vary within rather wide limits, depending inter alia on the unit activity (as hereinafter defined) of the soluble saccharifying enzyme starting material. However, in a preferred embodiment of this invention the weight ratio of saccharifying enzyme:casein is in the range of from 1:200 to 1:2, preferably 1:25 to 1:5, the amount of amyloglucosidase and maltogenic alpha-amylase being calculated on the basis of products having activites of 10,000 and 3,000 units per gram, respectively. Likewise, a preferred range of the weight ratio of saccharifying enzyme:egg albumen is from 1:5 to 1:0.05 and still more preferred is the range from 1:2 to 1:0.2.

According to a further aspect of this invention there is provided a process for the preparation of an immobilized saccharifying enzyme product in particulate form, the saccharifying enzyme being selected from the group consisting of amyloglucosidase and maltogenic alpha-amylase, which process comprises coating carrier particles of granular casein with a reaction mixture of the saccharifying enzyme, egg albumen and glutaraldehyde, whereby the granular casein becomes coated by a liquid-permeable proteinaceous layer, in which the saccharifying enzyme and egg albumen are cross-linked by reaction with glutaraldehyde.

In further detail, this process comprises the step of wetting a dry mixture of granular casein and egg albumen powder with an aqueous mixture consisting of the saccharifying enzyme and glutaraldehyde dissolved at pH 4–7, with vigorous stirring; followed by the step of maintaining the resulting wetted mixture in a quiescent state, usually at ambient temperature, to complete the combined carrier coating and protein cross-linking process. Wetting may be conducted either manually, for example by thorough mixing and kneading in a mortar, or mechanically, for example in a plough type horizontal mixer obtainable from Gebr. Lodige Maschinenbau G.m.b.H., Paderborn, West Germany, or a similar type of industrial mixing apparatus. Optionally, the albumen may be dissolved together with the enzyme and the glutaraldehyde instead of being mixed in the dry state with the casein.

The weight ratio of glutaraldehyde (usually added as a 50 percent (w/w) aqueous solution) to coating layer proteins (enzyme plus albumen) may vary considerably, the preferred range being 0.1 to 1. The water content of the aqueous solution is usually adjusted to be in the range of from 30 to 60 percent (w/w) of the total mixture.

The properties of the granular casein product selected as carrier material are significant for attaining the objects of this invention. Thus, the casein granules should possess sufficient physical stability to resist substantial deformation upon soaking under packed bed column conditions. In addition, the degree of swelling in water should be reasonably low, preferably not exceeding 200 percent. Exemplary of a product meeting such requirements is acid precipitated granular casein. Food grade products of this type, preferably having particle diameters in the range of from 100 to 500 microns are obtainable from various sources, for example from the French company Scerma S.A. Scanning electron microscope examination reveals that the surface of such particles has a very uneven and irregularly folded structure, bearing some resemblance to the macroscopic appearance of pumice. It is believed that a surface micro-structure of this type would expose a large number of glutaraldehyde binding sites.

It is essential for practising the present invention that a substantial fraction of the albumen used as binder protein be almost instantly soluble in water. Hence, the preferred grade of albumen is a generally available spray-dried product.

The mixing process may entail a certain degree of agglomeration of the coated particles, resulting upon completion of the cross-linking reaction in the formation of a coarse and lumpy product. This product may be subjected to disintegration, for example by granulation, to form a particulate product with particle sizes within a preferred range. Granulation may be effected on an oscillatory granulator of the type supplied by several companies (Diaf, Copenhagen or Manosty, Liverpool). The granulate product passing through the granulator screen, for example one with holes of 1-2 mm, may be freed of fine material by conventional means. The product so obtained may optionally be washed, followed by drying to a desired water content.

Prior to being used for a saccharification process, the dried enzyme product is usually conditioned by pre-soaking in an aqueous solution. At this stage and also subsequently during the initial phase of the use of the product, some leakage of enzyme activity may be observed. It has been found that inclusion of an additional cross-linking step, optionally in connection with the soaking process, may substantially reduce this loss of enzyme activity. Hence, according to one embodiment of this invention pre-treatment of the enzyme product is performed in an aqueous solution containing a suitable amount of glutaraldehyde, preferably 0.5 to 5 percent by weight, followed by removal of excess reagent by washing and, optionally, recovery of the dried product.

It has been found that pre-treatment of the enzyme product with a salt of sulphurous acid may effect a significant increase in the degree of conversion (as expressed in percent of dextrose equivalent or DE-value) of the saccharified product. A theory has been advanced that the sulphite action is an "opening up" of certain reticular structures involving the proteinaceous enzymatically active layer but apparently not affecting the bonding of the enzyme, thus facilitating the access of higher oligosaccharides to enzyme active sites. Accordingly, a further embodiment of this invention comprises treating the enzyme product with a dilute aqueous solution of sodium sulphite, preferably a 0.1-2 percent solution of pH 4-5. The sulphite treatment is preferably conducted at ambient temperature and terminated after 120 minutes by washing with water, optionally followed by recovery of the dried product. After the sulphite treatment enzyme leakage does not usually reappear.

The particulate enzyme products prepared according to the above procedure may be used in a batch-type saccharification process with separation and reuse of the enzyme product or in a continuous type of process in an enzyme reactor.

A preferred commercial amyloglucosidase product for the practice of this invention is obtained by cultivating strains belonging to the genera of Aspergillus or Rhizopus, e.g. *Aspergillus niger* or *Rhizopus delemar.* Likewise, preferred maltogenic alpha-amylases may be obtained from strains of *Aspergillus oryzea.*

Determination of Amyloglucosidase Activity

The unit activity of soluble amyloglucosidase as well as that of the immobilized enzyme, defined as the amount of enzyme or enzyme product which hydrolyses an aqueous solution containing 30 percent (w/v) of maltose, at an initial rate of 1 micromole of maltose per minute, is assayed under standard conditions, which are pH 4.5 and a temperature of 55.0° C. The activity of the immobilized enzyme is assayed batch-wise on a sample which is kept suspended by means of a shaking device.

Determination of Fungal Alpha-amylase Activity

The unit activity of soluble fungal alpha-amylase as well as that of the immobilized enzyme, defined as the amount of enzyme or enzyme product which hydrolyses an aqueous solution containing soluble starch (Merck Amylum solubile, DAB, Erg. B VI), (6.95 g per 1000 ml) at an initial rate of 5.26 mg of starch per hour, is assayed under standard conditions, which are pH 5.6–5.7, a temperature of 37.00° C ± 0.05° C and in the presence of 4.3 mmolar $Ca^{++}$ion. The formation of a blue colour with iodine is used to follow the reaction. During breakdown of the starch this colour becomes weaker and changes gradually to red-brown. The colour change is checked visually by comparison with coloured glass standards. The activity of the immobilized enzyme is assayed under conditions analogous to those indicated for amyloglucosidase.

Soluble saccharifying enzymes are commercially available. Exemplary of such products are AMYLO-GLUCOSIDASE NOVO 150 (an aqueous solution) and FUNGAMYL 1600 ® (a powder). Aqueous solution enzyme sources are usually converted into a spray-dried powder prior to being used for the purpose of this invention. Optionally, the drying process may be preceded by ultrafiltration, usually combined with a washing process to remove low molecular contaminants. By using such concentration and purification processes, all well known to the worker skilled in the art, a solid amyloglucosidase product with an activity of 5000 units per gram or higher is readily obtained.

FUNGAMYL 1600 has an activity of 1600 units per gram. The commercial product as such may serve as a satisfactory starting material. If desired, purification and concentration procedures may be used to increase the enzyme unit activity.

The over-all recovery of activity in the insolubilized saccharifying enzyme product will vary with the detailed parameters of the immobilization process, but is usually not less than 40 percent, and frequently higher.

The immobilized enzyme products of this invention may be employed on any oligosaccharide undergoing saccharification in the presence of the corresponding soluble enzyme. Exemplary of preferred substrates are dextrins obtained by acid and/or enzyme liquefaction of starch and having DE-values in the range of from 5 to 40; high maltose syrups (DE-values from 35 to 60); and residual oligosaccharides occuring in mother liquors from dextrose crystallisation or in raffinates obtained from fructose-glucose fractionation. The immobilized saccharifying enzyme products are particularly applicable to saccharification of dextrin solutions having a dry solids content in the range of from 20 to 55 percent (w/v).

The following examples further illustrate the present invention.

EXAMPLE I

A relatively coarse grade granular hydrochloric-acid-precipitated casein (9 g of "caseine alimentaire" (Scerma S.A., France), consisting of 100-500 micron particles, the 300-500 micron fraction being about 60 percent) was mixed with commercial spray-dried egg albumen (1.2 g). To this mixture was added a pre-mixed solution of amyloglucosidase powder (6.5 ml of 18.5 percent (w/v) aqueous solution, containing a total of 12.500 amyloglucosidase units) and glutaraldehyde (1.2 ml of 50 percent (w/w) aqueous solution). The amyloglucosidase powder was an ultrafiltrated, spray-dried product prepared from AMYLOGLUCOSIDASE NOVO (NOVO INDUSTRI A/S, Denmark). The mixture was kneaded carefully in a mortar and then allowed to stand at room temperature for 1 hour. The resulting aggregate was disintegrated by mortaring to form a granular product which was allowed to dry at room temperature for one day.

The dried granular product (11.4 g) had an activity of 425 units per g, thus representing a recovery after immobilization of 38.8 percent.

EXAMPLE II

Granular acid-precipitated casein (1500 g of type M60 (Scerma S.A.), consisting of 100-500 micron particles, the 150-350 micron fraction being about 70 percent) was mixed in the dry state with commercial spray-dried albumen (120 g) in a 20 liter plough-type horizontal mixer (Gebr. Lodige Machinenbau, G.m.b.H., West Germany).

An ultrafiltrated concentrate of amyloglucosidase, prepared from AMYLOGLUCOSIDASE NOVO (650 g of a solution having a dry matter content of about 25 percent and containing ca. 3200 units of soluble amyloglucosidase per g of concentrate) was mixed thoroughly with glutaraldehyde (180 ml of a 50 percent (w/w) aqueous solution) at pH 4.9 and a temperature of 18° C, whereafter the resulting solution was poured into the mixing apparatus. Vigorous mixing was continued for an additional 0.5 to 1 minute, followed by removal of the wetted particulate product from the mixer. The moist product was left quiescent for about 45 minutes to complete the cross-linking process, whereby lumps of aggregated particles were formed. Granulation of the product was conducted on an oscillatory granulator (for example of the type supplied by Diaf A/S, Copenhagen) provided with a 1.5 mm diameter screen.

The granulate was washed with de-ionized water (10 l) for 10 minutes, recovered by filtration and then subjected to fluid-bed drying. The dried product (1600 g, 450 amyloglucosidase units per g) was freed of fines by sieving.

EXAMPLE III

A solution of spray-dried amyloglucosidase powder (105 g, activity: 11.400 units per g, prepared as described in Example I) and spray-dried albumen (105 g) was prepared in tap water (400 6°-and left overnight in the refrigerator at 6-7° C. The pH of the solution was 5.4.

Glutaraldehyde (100 ml of 50 percent (w/w) aqueous solution) was then added and the resulting solution was transferred in the course of 3 minutes to a vigorously stirred batch of granular hydrochloric-acid-precipitated casein (725 g of the same grade as that used in Example I). Mixing was conducted in an industrial mixer of the same type as that of EXAMPLE II. Vigorous stirring of the reaction mixture was continued for an additional few minutes, whereafter it was left quiescent until the cross-linking reaction was completed after about 1 hour. The resulting aggregated and lumpy product was granulated on an oscillatory granulator through a 2 mm diameter screen.

The granulate was washed with an aqueous solution of sodium acetate (pH 4.2), followed by vacuum drying at 35° C.

The dried granular product (925 g) had an activity of 800 units per g, representing a recovery after immobilization of 67.8 percent.

EXAMPLE IV

The immobilized amyloglucosidase product prepared according to Example III (20 g) was soaked for one hour at ambient temperature in an aqueous solution of glutaraldehyde (500 ml of 1 percent solution adjusted to pH 7), followed by recovery of the dried product (20 g).

The activity of this product was 625 units per g, thus representing a recovery of 78 percent from the second immobilization step and an overall recovery from soluble amyloglucosidase of 53 percent.

EXAMPLE V

An aqueous solution of maltogenic alpha-amylase (2 ml of 5 percent (w/v) solution of FUNGAMYL 1600 (NOVO INDUSTRI A/S, Denmark) in de-ionized water at pH 6.2) was mixed with an aqueous solution of glutaraldehyde (0.3 ml of 50 percent (w/w) solution) and then quickly added to a dry mixture of granular acid-precipitated casein (4.0 g of type M60) and commercial spray-dried egg albumen (0.5 g). After thorough kneading in a mortar the resulting product was left for 1 hour at room temperature. Lumps were disintegrated by mortaring whereafter the product was allowed to dry at room temperature for 1 day.

EXAMPLE VI

A 15 mm inner diam. jacketed column, maintained at 55° C, was loaded with the immobilized amyloglucosidase product (5.7 g) prepared according to Example I.

A down-flow feed consisting of a 30 percent (w/v) commercial acid/enzyme-hydrolyzed dextrin (CPC Snow Flake Maltodextrin 01915 of D.E. 20) having the following approximate composition:

|  | percent |
|---|---|
| glucose ($DP_1$) | 4 – 5 |
| disaccharides ($DP_2$) | 8 – 9 |
| trisaccharides ($DP_3$) | 6 – 7 |
| tetra-and oligosaccharides ($DP_4+$) | 79 – 82 | to which was added 0.2 percent (w/v) sodium sulphite followed by adjustment of pH to 4.5, was applied to the column at a constant flow rate of 15 ml per hour.

The effluent was analyzed by high pressure liquid chromatography (HPLC) to give the following results:

| Days | $DP_1$ percent | $DP_2$ percent | $DP_3$ percent | $DP_{4+}$ percent | Calculated D.E. |
|---|---|---|---|---|---|
| 1 | 92.0 | 5.6 | 0.7 | 1.7 | 95.3 |
| 4 | 93.2 | 4.2 | 0.6 | 2.0 | 95.8 |
| 5 | 92.9 | 3.9 | 0.7 | 2.5 | 95.4 |
| 7 | 93.6 | 3.2 | 0.6 | 2.5 | 95.8 |
| 9 | 93.3 | 3.1 | 0.7 | 2.9 | 95.5 |
| 11 | 92.6 | 3.2 | 0.8 | 3.3 | 94.9 |
| 13 | 92.6 | 2.9 | 0.9 | 3.6 | 94.9 |

EXAMPLE VII

A 25 mm inner diam. jacketed column, maintained at 55° C, was loaded with the immobilized amyloglucosidase product (20 g) prepared according to Example II. An up-flow substrate feed having the same concentration, composition and pH as that used in Example VI was applied to the column at a constant flow rate of 50 ml per hour. The glucose content (percent $DP_1$) was analyzed by the hexokinase method to give the following results:

| Days | percent $DP_1$ |
|---|---|
| 1 | 89.0 |
| 4 | 93.6 |
| 6 | 93.6 |
| 8 | 93.1 |

EXAMPLE VIII

A 25 mm inner diam. jacketed column, maintained at 55° C, was loaded with the immobilized amyloglucosidase product (25 g) prepared according to Example II. An up-flow substrate feed of the same composition as that used in Example VI was applied to the column. The feed (pH 4.5) had a dry solids content of 30 percent (w/w) and potassium sorbate (2 g per liter) was added as a preservative. The flow rate was adjusted so as to maintain an approximately constant degree of conversion.

The effluent was analyzed by means of HPLC to give the following conversion to glucose ($DP_1$) with time:

| Days | $DP_1$ percent | Flow rate ml/hour |
|---|---|---|
| 1 | 92.6 | 115 |
| 2 | — | 112 |
| 3 | 92.4 | 101 |
| 4 | 92.0 | 82 |
| 5 | 92.2 | 75 |
| 6 | 92.3 | 70 |
| 7 | 92.1 | 66 |
| 8 | 92.6 | 64 |
| 9 | — | 60 |
| 10 | 92.0 | 57 |

After completion of the run no changes were observed in the hardness or other physical properties of the column material.

EXAMPLE IX

By using the procedure of Example VII, but substituting the immobilized amyloglucosidase product of Example II with that prepared according to Example IV, the following results were obtained:

| Days | percent $DP_1$ |
|---|---|
| 1 | 90.3 |
| 2 | 92.9 |
| 4 | 93.7 |
| 13 | 93.3 |

Example X

The immobilized maltogenic alpha-amylase prepared according to the procedure of Example V (4 g) was packed into a jacketed column maintained at 45° C, and a down-flow feed of commercial dextrin (CPC Snow Flake Maltodextrin 01913) containing 30 percent (w/v) dry solids and sodium sulphite (0.2 percent) as a preservative was applied. The pH of the feed was adjusted to 4.5 and the flow rate to 15 ml per hour. The following table shows the composition of the column effluent; $DP_2$ mainly representing the maltose content:

| Days | $DP_1$ percent | $DP_2$ percent | $DP_3$ percent | $DP_{4+}$ percent | Calculated D.E. |
|---|---|---|---|---|---|
| 1 | 5.3 | 45.4 | 21.0 | 28.3 | 42.5 |
| 2 | 5.0 | 44.9 | 21.6 | 28.5 | 42.1 |
| 3 | 4.7 | 44.1 | 22.0 | 29.2 | 41.7 |
| 4 | 4.4 | 43.5 | 22.7 | 29.4 | 41.2 |

EXAMPLE XI (A) A 15 mm inner diam. jacketed column, maintained at 55° C was loaded with immobilized amyloglucosidase (12 g) prepared according to the method of Example II.

A down-flow feed of dextrin (31 percent (w/w) based on dry matter content), prepared by liquefaction of starch with TERMAMYL ® L60 (NOVO INDUSTRI A/S, Denmark) and having the following composition:

| | percent |
|---|---|
| glucose ($DP_1$): | 1 |
| disaccharides ($DP_2$): | 7–8 |
| trisaccharides ($DP_3$): | 10–12 |
| tetra- and oligosaccharides ($DP_{4+}$): | 79–82 |
| D.E. | 21 | was applied to the column.

The feed contained sodium sulphite (0.2 percent (w/v)) as a preservative and had a pH of 4.5. The flow was regulated to maintain a constant degree of conversion (in terms of percent $DP_1$). The effluent was analyzed by HPLC to give the following results:

| Days | $DP_1$ percent | $DP_2$ percent | $DP_3$ percent | $DP_{4+}$ percent | Flow rate ml/hour |
|---|---|---|---|---|---|
| 3 | 92.1 | 4.2 | 0.7 | 3.1 | 35 |
| 7 | 92.3 | 3.6 | 0.8 | 3.3 | 33 |
| 14 | 92.2 | 3.6 | 0.7 | 3.5 | 27 |
| 28 | 92.4 | 3.1 | 0.9 | 3.6 | 18 |
| 56 | 92.1 | 3.3 | 0.8 | 3.7 | 15 |

(B) A dextrin substrate prepared according to the method described under (A) and having the following composition:

| | percent |
|---|---|
| glucose ($DP_1$): | 1.1 |
| disaccharides ($DP_2$): | 6.8 |

-continued

| | percent |
|---|---|
| trisaccharides (DP$_3$): | 11.0 |
| tetra- and oligosaccharides (DP$_{4+}$): | 81.0 | was treated with 0.01 percent (based on total dry solids) of maltogenic alpha-amylase (FUNGAMYL 1600, NOVO INDUSTRI A/S) at pH 5.0 and 50° C for 2 hours. After treatment the substrate had the following composition:

| | percent |
|---|---|
| glucose (DP$_1$): | 1.3 |
| disaccharides (DP$_2$): | 13.9 |
| trisaccharides (DP$_3$): | 22.3 |
| tetra- and oligosaccharides (DP$_{4+}$): | 62.5 |

Each of two 15 mm inner diam. jacketed columns, maintained at 55° C, were loaded with immobilized amyloglucosidase (10 g, prepared according to Example II). Down-flow feeds consisting of 30 percent (w/w) of the two types of dextrin, prepared as described above, to which was added 0.2 percent (w/v) of potassium sorbate, followed by adjustment of pH to 4.5, were applied to the columns. The following results were obtained:

| | Dextrin | |
|---|---|---|
| Feed | before FUNGAMYL treatment | after FUNGAMYL treatment |
| Maximum DX-value of effluent, percent | 92.7 | 93.3 |

EXAMPLE XII

Portions (10 g) of immobilized amyloglucosidase, prepared according to the method of Example II, were soaked in 100 ml solutions containing different concentrations of sodium sulphite. The pH of the solution was adjusted to 4.5 by the addition of acetic acid. After soaking for 2 hours at ambient temperature the enzyme samples were washed with de-ionized water and packed into 15 mm inner diam. jacketed columns maintained at 55° C.

Down-flow feeds consisting of dextrin (30 percent (w/w)), prepared according to the method of Example XI A to which was added potassium sorbate (0.2 percent (w/v)) followed by pH adjustment to 4.5 were applied to the column.

By adjusting the flow rate of each column to give the maximum DX-value of the effluent the following results were obtained:

| Sodium sulphite g/100 ml | 0 | 0.01 | 0.1 | 0.2 | 0.5 | 1.0 |
|---|---|---|---|---|---|---|
| Maximum DX | 90.3 | 90.2 | 91.2 | 91.7 | 91.9 | 92.4 |

EXAMPLE XIII

The collected high maltose (D.E. about 42) effluent from the immobilized FUNGAMYL column of Example X was used as a feed for the immobilized amyloglucosidase column of Example VI. The flow rate was adjusted (to 73 ml per hour) to yield an effluent having the following composition of a high conversion (D.E. about 65) syrup:

| | percent |
|---|---|
| glucose (DP$_1$): | 38.1 |
| disaccharides (DP$_2$): | 39.6 |
| trisaccharides (DP$_3$): | 2.8 |
| tetra- and oligosaccharides (DP$_{4+}$): | 19.6 |

EXAMPLE XIV

A 25 mm inner diam. jacketed column, maintained at 55° C, was loaded with immobilized amyloglucosidase product (20 g) prepared according to Example III.

An up-flow substrate feed consisting of the mother liquor (or raffinate) obtained from fructose-glucose fractionation and having the following composition:

| | percent |
|---|---|
| fructose | 3.25 |
| glucose | 85.71 |
| disaccharides | 9.17 |
| trisaccharides | 1.42 |
| higher saccharides | 0.54 | and pH adjusted to 4.5 was applied to the column at a flow rate of 250 ml per hour at a concentraion of 25 percent (w/w). The composition of the effluent, determined by HPLC was shown to be:

| | percent |
|---|---|
| fructose | 3.25 |
| glucose | 91.16 |
| disaccharides | 4.14 |
| trisaccharides | 1.15 |
| higher saccharides | 0.30 |

What is claimed:

1. An immobilized saccharifying enzyme product in particulate form, the saccharifying enzyme being selected from the group consisting of amyloglucosidase and maltogenic alpha-amylase, which product comprises carrier particles of granular casein having a coating of a liquid-permeable proteinaceous layer comprising the saccharifying enzyme and egg albumen cross-linked by reaction with glutaraldehyde.

2. The product of claim 1, in which the weight ratio of the amount saccharifying enzyme-casein is in the range of from 1:200 to 1:2.

3. The product of claim 1, in which the weight ratio of the amount of saccharifying enzyme:casein is in the range of from 1:25 to 1:5.

4. The product of claim 1, in which the weight ratio of the amount of saccharifying enzyme:albumen is in the range of from 1:5 to 1:0.05.

5. The product of claim 1, in which the weight ratio of the amount of saccharifying enzyme:albumen is in the range of from 1:2 to 1:0.2.

6. The product of claim 1, in which the particle diameter of the granular casein is in the range of from 100 to 500 microns.

7. The product of claim 1, in which the granular casein is acid-precipitated casein.

8. A process for the preparation of an immobilized saccharifying enzyme product in particulate form, the saccharifying enzyme being selected from the group consisting of amyloglucosidase and maltogenic alpha-amylase, which process comprises coating carrier particles of precipitated casein with a reaction mixture of the saccharifying enzyme, egg albumen and glutaraldehyde, whereby the granular casein becomes coated by a liquid-permeable proteinaceous layer, in which the saccharifying enzyme and egg albumen are cross-linked by reaction with the glutaraldehyde.

9. The process of claim 8, in which the weight ratio of the amount of saccharifying enzyme:casein is in the range of from 1:200 to 1:2.

10. The process of claim 8, in which the weight ratio of the amount of saccharifying enzyme:casein is in the range of from 1:25 to 1:5.

11. The process of claim 8, in which the weight ratio of the amount of saccharifying enzyme:albumen is in the range of from 1:5 to 1:0.05.

12. The process of claim 8, in which the weight ratio of the amount of saccharifying enzyme:albumen is in the range of from 1:2 to 1:0.2.

13. The process of claim 8, in which the particle diameter of the granular casein is in the range of from 100 to 500 microns.

14. The process of claim 8, in which the granular casein is acid-precipitated casein.

15. The process of claim 8, in which the weight ratio of glutaraldehyde to the enzyme plus albumen incorporated into the proteinaceous layer is in the range of from 0.1 to 1.

16. The process of claim 8, in which the immobilized saccharifying enzyme product is treated with an aqueous solution of glutaraldehyde.

17. The process of claim 8, in which the immobilized saccharifying enzyme product is treated with an aqueous solution of a salt of sulphurous acid.

18. The process of claim 16, in which the immobilized saccharifying enzyme product is thereafter treated with an aqueous solution of a salt of sulphurous acid.

* * * * *

UNITED STATES PATENT AND TRADEMARK OFFICE
CERTIFICATE OF CORRECTION

PATENT NO. : 4,116,771

DATED : Sept. 26, 1978

INVENTOR(S) : Shmuel Amotz et al

It is certified that error appears in the above-identified patent and that said Letters Patent are hereby corrected as shown below:

On the title sheet, add the following:

[30] Foreign Application Priority Data

July 2, 1976 [GB] United Kingdom 27749/76.

Signed and Sealed this

Twenty-fourth Day of April 1979

[SEAL]

Attest:

RUTH C. MASON
Attesting Officer

DONALD W. BANNER
Commissioner of Patents and Trademarks